US011932840B2

(12) United States Patent
Scaglione et al.

(10) Patent No.: US 11,932,840 B2
(45) Date of Patent: Mar. 19, 2024

(54) BIOREACTOR AND METHOD OF USE OF SUCH BIOREACTOR (71) Applicant: REACT4LIFE S.R.L., Genoa (IT)

(72) Inventors: Silvia Scaglione, Genoa (IT); Maurizio Aiello, Genoa (IT); Marta Maria Cavo, Genoa (IT)

(73) Assignee: REACT4LIFE S.R.L., Genoa (IT)

( * ) Notice: Subject to any disclaimer, the term of this patent is extended or adjusted under 35 U.S.C. 154(b) by 488 days.

(21) Appl. No.: 16/478,084

(22) PCT Filed: Jan. 15, 2018

(86) PCT No.: PCT/IB2018/050236
§ 371 (c)(1),
(2) Date: Jul. 15, 2019

(87) PCT Pub. No.: WO2018/130998
PCT Pub. Date: Jul. 19, 2018

(65) Prior Publication Data
US 2019/0359926 A1 Nov. 28, 2019

(30) Foreign Application Priority Data
Jan. 16, 2017 (IT) .......................... 102017000004017

(51) Int. Cl.
C12M 1/00 (2006.01)
C12M 1/12 (2006.01)
C12M 1/34 (2006.01)

(52) U.S. Cl.
CPC .......... C12M 23/34 (2013.01); C12M 1/3407 (2013.01); C12M 23/38 (2013.01); C12M 25/06 (2013.01); C12M 29/04 (2013.01)

(58) Field of Classification Search
CPC .... C12M 23/34; C12M 1/3407; C12M 23/38; C12M 25/06; C12M 29/04
See application file for complete search history.

(56) References Cited

U.S. PATENT DOCUMENTS 5,536,405 A * 7/1996 Myrna ................... B01D 65/00
210/231
5,583,037 A * 12/1996 Mussi ................... C12M 35/08
435/297.5

(Continued)

FOREIGN PATENT DOCUMENTS

DE 195 30 556 C1 9/1996
EP 0 112 155 A2 6/1984
WO 2004/044120 A2 5/2004

OTHER PUBLICATIONS

International Search Report and Written Opinion of the International Searching Authority for corresponding International Patent Application No. PCT/IB2018/050236 dated May 9, 2018, 10 pages.

Primary Examiner — William H. Beisner
Assistant Examiner — Danielle B Henkel
(74) Attorney, Agent, or Firm — Merchant & Gould P.C.

(57) ABSTRACT

A bioreactor includes a container (1) composed of at least one side wall (11), a bottom wall (12) and an opening (13) closed by a cap (14), such to identify an inner chamber. An intermediate wall (2) is inside the inner chamber, to divide the inner chamber in an upper chamber (31) and a lower chamber (32). The intermediate wall (2) has at least one hole (21). The intermediate wall (2) has at least one region resting on the bottom wall and/or the side wall and provides at the hole (21) at least one housing seat (26) for a membrane (22).

20 Claims, 9 Drawing Sheets (56) References Cited

U.S. PATENT DOCUMENTS

| | | | |
|---|---|---|---|
| 9,371,508 B2* | 6/2016 | Angeloni Suter | C12M 23/00 |
| 2003/0215940 A1* | 11/2003 | Lacey | C12M 23/12 |
| | | | 435/305.2 |
| 2004/0091397 A1* | 5/2004 | Picard | B01L 3/50853 |
| | | | 422/400 |
| 2007/0042490 A1* | 2/2007 | Welter | C12N 5/0655 |
| | | | 435/325 |
| 2008/0076170 A1* | 3/2008 | Annala | C12M 25/04 |
| | | | 435/305.1 |
| 2012/0183987 A1 | 7/2012 | Gevaert et al. | |
| 2014/0065660 A1 | 3/2014 | Kim et al. | |
| 2016/0228606 A1* | 8/2016 | Danti | A61L 27/3645 |
| 2022/0372419 A1* | 11/2022 | Hori | C12M 25/04 |

* cited by examiner

BIOREACTOR AND METHOD OF USE OF SUCH BIOREACTOR

This application is a National Stage Application of PCT/IB2018/050236, filed 15 Jan. 2018, which claims benefit of Serial No. 10/2017000004017, filed 16 Jan. 2017 in Italy and which applications are incorporated herein by reference. To the extent appropriate, a claim of priority is made to each of the above-disclosed applications.

BACKGROUND OF THE INVENTION

The present invention relates to a bioreactor comprising a container composed of at least one side wall, a bottom wall and an opening closed by a cap, such to identify an inner chamber.

Inside the inner chamber there is provided an intermediate wall intended to divide the inner chamber in an upper chamber and a lower chamber, the intermediate wall having at least one hole.

The configuration just described is that of some known prior art bioreactors, namely those apparatuses able to provide an environment suitable for the growth of biological samples.

Particularly the invention relates to those bioreactors used to carry out diffusion studies for emulating biological interface processes.

Known prior art bioreactors have a membrane intended to simulate an interface tissue that divides the upper chamber from the lower chamber: for example molecules are inserted in the upper chamber and the passage of such molecules from the upper chamber to the lower chamber is studied.

Although the widespread use, known prior art bioreactors are limited to few applications, above all due to the fact of being difficult to adapt them to the several configurations of the analyses to be carried out.

Due to their small dimensions they cannot receive therein three-dimensional biological material. Moreover the membrane used in such bioreactors allows only particles/molecules to pass through.

Such limitation is an important drawback above all in particular applications such as the analysis of diffusion of tumor cells, where, in order to guarantee valid analysis results, there is the need of using tumor cells cultured in a three-dimensional clinically relevant size matrix such to give rise to an artificial tumor, and namely much greater than simple cells.

Moreover in confirmation of their poor adaptability, known prior art bioreactors are comparable to "disposable" devices, they do not provide removable, replaceable, sterilizable and therefore reusable parts or parts adaptable to the different operating configurations.

Therefore there is the need not satisfied by known prior art devices to provide a bioreactor overcoming the above mentioned drawbacks and having characteristics allowing it to meet a different range of analyses to be carried out, by simply modifying its components.

SUMMARY OF THE INVENTION

The present invention achieves the above objects by providing a bioreactor such as described hereinbefore, wherein the intermediate wall has at least one region resting on the bottom wall and/or side wall and wherein the intermediate wall provides at the hole alternatively a membrane or a housing seat, intended to house at least one membrane.

The membrane obviously is intended to allow cells, molecules, particles and/or fluids to pass from the upper chamber to the lower chamber and vice versa.

Therefore a bioreactor is provided having a replaceable, sterilizable and reusable or disposable membrane, depending on the applications.

The characteristic configuration of the intermediate wall allows a housing seat to be created wherein the membrane can be housed and easily replaced, without necessarily being fastened to the intermediate wall.

Such configuration allows the membrane to be replaced and the most useful type of it to be selected depending on applications.

As it will be clear from some embodiments, in a variant embodiment, the membrane can rest inside the housing seat, without the need of fastening means, not only guaranteeing the membrane to be easily replaced, but also guaranteeing its positioning to be adjusted.

Moreover the bioreactor of the present invention is not limited to a single type of membrane, but, since it is replaceable, the membrane can be made ad hoc for the type of application.

The membrane can be made in any of the manners known in prior art.

For example the membrane can be composed of a polymer material obtained by electrospinning process.

Likewise the membrane can be composed of a polymer, metal material or any material, obtained through a 3D printing process. As an alternative it can be a membrane available on the market or any other porous and/or permeable septum that can act as a membrane. It is clear how a membrane of said type can be adapted to the different operating needs: the disclosed processes allow not only dimensions of the membrane to be changed, but also the porosity and/or permeability of the membrane to be adjusted.

The membrane of the bioreactor of the present invention therefore allows all the processes occurring at the interface of a tissue to be simulated.

Moreover both electrospinning and 3D printing allows membranes with different porosity to be obtained while maintaining a suitable mechanical strength and biocompatibility.

Advantageously it is possible to provide a coating (functionalization) for the membrane made of protein material, such as gelatin, collagen or other polymers, or biological material (cell monolayer).

For example it is possible to provide a membrane to be coated with collagen and other extracellular matrix proteins of the epithelium, on which epithelial cells are cultured for reconstructing endothelium layers in vitro.

Regardless of the realization, the important aspect in this case is the possibility of replacing and modifying the membrane on the basis of operating needs.

As an alternative or in combination the membrane can be composed at least partially of cells by living tissues.

For example the membrane can be composed epithelial tissue.

In this case the bioreactor of the present invention can be used to analyse the passage and/or absorption of cells, biological molecules or radiations or cell clusters, for cosmetic and/or dermatologic purposes.

According to a further embodiment, the membrane is composed of gastrointestinal epithelial tissue and/or tissue of interest of the digestive system.

In this case the bioreactor of the present invention can be used to analyze the passage and/or absorption of cells, biological molecules or radiations or cell clusters for nutraceutical, food purposes or for human, animal or vegetable digestive processes.

According to a further embodiment the membrane can be composed of pulmonary epithelial tissue.

In this case the bioreactor of the present invention can be used to analyse the passage and/or absorption of cells, biological molecules or radiations or cell clusters for respiratory system purposes.

Moreover the membrane can be composed of epithelial tissue of different type (cornea, nasal mucous membrane, lingual mucosa) or other type of tissue (hair).

In this case the bioreactor of the present invention can be used to analyse the passage and/or absorption of cells, biological molecules or radiations or cell clusters for cosmetic, biotechnology, physiologic purposes.

In order to give to the bioreactor of the present invention a high adaptability, the present invention provides two main embodiments of the bioreactor of the present invention that will be described below.

Regardless of the realization, the bioreactor of the present invention allows the positioning, above all height positioning of the membrane to be adjusted, in addition to allow it to be easily replaced as described before.

The possibility of height adjustment of the membrane is essential to give to the bioreactor greater adaptability.

Therefore the membrane can be moved on the basis of analyses to be made, of dimensions of the samples to be inserted in the upper chamber and/or lower chamber and of flow conditions to be applied.

As it will be described below, the two embodiments of the bioreactor provide a height adjustment of the membrane and of the intermediate wall with the membrane respectively.

According to a first embodiment it is possible to provide one or more support elements, on which the membrane is supported, whose thickness changes the height positioning of the membrane.

On the contrary the second embodiment provides to use a cup element to make the intermediate wall, which has the membrane at the bottom: the height displacement of the cup element causes the membrane to be consequently displaced.

Therefore it results in an integral construction of membrane and cup element, thus the displacement of the membrane can be caused not only by the height displacement of the cup element, but also by a change in the shape and dimensions thereof, such as for example increase, decrease or narrowing of the side walls of the cup, that can even require the shape of the membrane to be changed.

Advantageously according to a preferred embodiment, there is provided a fluidic circuit connected to the bioreactor, such to better simulate tissues and to perform "dynamic" analyses, with a fluid flow (air/liquid).

In this case the side wall delimiting the lower chamber and/or the side wall delimiting the upper chamber and/or the cap and/or the bottom wall have at least one inlet port and at least one outlet port for the connection of corresponding fluidic circuits.

As it will be clear from the embodiments annexed to the present patent application, it is possible to provide two separate circuits, one for the upper chamber and one for the lower chamber.

In order to maintain unchanged the characteristics of the variability of volume of the chambers obtained by height adjustment of the intermediate wall or membrane, advantageously the inlet port and the outlet port for the upper chamber can be placed near the opening, while the inlet port and the outlet port for the lower chamber are placed near the bottom wall.

Thus the intermediate wall or the membrane are free to change their position without interfering with the fluid flow.

As set forth, the "free" positioning of the membrane is the inventive concept of the present invention: the particular configuration of the intermediate wall does not necessarily require means for fastening the membrane.

Therefore there is no need to use clamps or clips that require the use of membranes with a specific stiffness level.

It is possible to provide the membrane to be maintained fixed by means of gaskets, or glued by surgical sealants or can be inserted in commercial inserts. Anyway the bioreactor of the present invention allows any type of membrane to be housed such to have the required fluid flow thereon.

For example as regards studies related to lung diffusions, it is necessary to provide a fluid flow flush with the cellularized membrane to recreate physiological conditions present in alveoli of the lung and only the height adjustment of the membrane can guarantee such condition, while maintaining a high adaptability of the bioreactor.

As it is clear, also on the basis of the embodiments described below, the bioreactor of the present invention in addition to allow interchangeability and positioning adjustment of the membrane to be guaranteed, it allows membranes both with variable shapes and thicknesses to be housed, as well as more than one membrane to be housed.

According to a further variant embodiment, it is possible to provide a plate element with a specific thickness and shape, intended to be placed in contact with the bottom wall such to limit the volume of the lower chamber.

The reduction in volume of the lower chamber allows the reduction of growth factors or drugs amount, which are particularly expensive, as well as it allows the various physiological conditions to be emulated, for example the capillary circuit (small caliber) or aorta (larger caliber).

For a fine adjustment of the volume of the lower chamber, it is possible to provide a plurality of plate elements that can be stacked on each other till reaching the desired volume within the chamber.

In this case the inlet and outlet ports for the connection to the fluidic circuit of the lower chamber can be provided near the intermediate wall.

As said above, there is provided at least one fluidic circuit connected to the lower chamber and/or to the upper chamber to perform dynamic analyses.

In this case the fluidic circuit has at least one pump, a delivery pipe and a return pipe.

In order to sample the circulating fluid and to carry out the analyses, there is provided a valve, for example a three-way valve, placed on the delivery pipe and/or return pipe.

Finally according to a possible embodiment, it is possible to provide the bioreactor of the present invention to have one or more sensors inside or outside the lower chamber and/or upper chamber and/or walls delimiting the bioreactor.

Due to the above advantages, the present invention relates also to a system for analysing passage of cells, molecules, particles, compounds, substances, nutrients, pollutants, growth factors, cell groups (clusters), drugs and/or matter of any kind, or electromagnetic radiations.

The system provides to use a bioreactor connected through a fluidic circuit to any collection system, allowing the collection of the fluid passing in the upper or lower chamber of the bioreactor, such to be analysed later.

In a preferred variant embodiment, the collection system is composed of a further bioreactor.

Particularly, according to such configuration, the system provides at least two bioreactors, made according to one or more of the characteristics described above, connected through a fluidic circuit.

Moreover the two bioreactors can be connected in series with each other, such that the matter listed above and/or the fluid contained therein are obliged to pass through the membranes and/or the chambers following a path determined beforehand, for example if the inlet and outlet ports of the lower chamber of a bioreactor are connected to outlet and inlet ports respectively of the upper chamber of the other bioreactor.

Alternatively the two bioreactors can be connected in parallel with each other, such that the matter listed above and/or the fluid can follow different possible paths through the membranes and/or chambers, for example if the inlet and outlet ports of the upper chamber of a bioreactor are connected to the outlet and inlet ports respectively of the upper chamber of the other bioreactor, while the lower chambers are not connected with each other and receive the matter only from their own upper chamber.

In addition to the advantageous aspects related to bioreactors and also related to the system of the present invention as it will be clear from the embodiments described and shown below, such system allows also the passage of cells and their migration and/or adhesion to a sample tissue present in the lower chamber of the second bioreactor to be analysed.

Moreover as it will be clear by the method of the present invention, the possibility of having two bioreactors in series is the only manner to recreate metastasis in vitro, such to obtain a clinical model currently not available in prior art, that provides to study intravasation and extravasation phenomena that is the passage of two epithelial membranes.

It is possible to recreate in the upper chamber of a bioreactor the environment of the primary tumor where tumor cells are cultured in vitro/ex vivo and grown, for example a human tumor biopsy for diagnostic and/or therapeutic and/or research use, or primary cells or liquid biopsies or stabilized lines or other inside a natural or artificial biological tissue.

Such model of primary tumor is cultured in the bioreactor in contact with the membrane that can have different porosity and/or permeability levels, and that can be made of inorganic or organic material, functionalized or not functionalized with cells (for example endothelial cells) to recreate the wall of blood vessels.

Likewise, the other bioreactor can house the same membrane and in the lower chamber can recreate the metastatic microenvironment. Such configuration makes it possible to observe ex vivo/in vitro the migration of tumor cells from the primary tumor, their intravasation, that is the passage through the endothelial barrier, their circulation in the flow between the two bioreactors, that recreates the blood flow, their extravasation, that is the passage through the endothelial barrier to reach the metastatic site. Such metastasis model allows different types of cells to be maintained in physically isolated environments, and allows the onset of metastases from primary tumor to be observed, therefore providing a platform for:
- toxicity, safety and efficacy tests of new therapeutic solutions, new chemotherapeutics
- drug-discovery and pharmacokinetic tests Such configuration, together with the method of use of the bioreactors, allows also to carry out drug repositioning. Particularly it allows efficacy studies of drugs, already known in prior art for other pathologies to be studied on new pathologies recreated in vitro/ex vivo in the bioreactor of the present invention.

It is further possible to work with different flow and viscosity conditions thereof, recreating different physiological/pathological contexts.

Moreover it is possible to perform therapy, when for example the biopsy of an oncologic patient is cultured in the bioreactor and different drugs and/or experimental therapeutic approaches are tested and their efficacy is verified ex vivo/in vitro.

Due to what just described, the present invention finally relates to a method for the analysis of the passage of cells, molecules, particles, compounds, substances, nutrients, pollutants, growth factors, cell groups (clusters), drugs and/or matter of any kind, or electromagnetic radiations.

The method provides to use at least one bioreactor as described above.

The method further provides the following steps:
a) generation of a fluid flow in the lower and/or upper chamber;
b) collection and analyses of a part of the fluid flowing in the chambers and of the matter (listed above) contained therein or of the transmitted radiations.

Unlike prior art known systems and methods, that treat the passage of solutes and substances, the method and the bioreactor of the present invention allow also the passage of cells to be analysed by using three-dimensional biological material, where a plurality of cells is present, placed in the bioreactor.

Therefore it is possible to study mechanisms that involve cell passages, such as passage of tumor cells from the tissue representing the primary tumor to the blood flow (intravasation) and to the target tissue of the metastasis (extravasation).

According to a possible embodiment, there is provided a step inserting biological material in the upper chamber and/or lower chamber, there being provided a following step analysing the biological material after the effect of the passage of fluid and/or molecules contained therein and/or the passed radiation.

It is specified that the biological material can be composed of biological material (biopsies) samples or material artificially recreated by adding cells.

In the case for example of the analysis of the passage of tumor cells, it is possible to recreate a tissue or an organ suffering from a tumor through a carrier material having suspended and/or adherent tumor cells.

Such material is inserted in the upper chamber in contact with the membrane.

Then a fluid flow is established in the device and the number of cells leaving the tumor, actively passing through the membrane and arriving in the fluidic circuit is evaluated, by drawing a part thereof through the three-way valve.

On the basis of the desired environment it is possible to provide to generate a fluid flow also in the upper chamber.

Advantageously there is provided a step adjusting the velocity of the fluid flow, even not constant over time, that can be different for the two chambers.

Such arrangement makes it possible to increase the possibility of simulating various environments where the cell passage has to be studied.

Optional characteristics of the bioreactor, of the method and system of the present invention are in the annexed dependent claims, which are an integral part of the present description.

Finally the method of the present invention therefore allows a material and a membrane to be maintained in contact which can correspond in the reality to a tumor and to an interface tissue, such as endothelium, inside a dynamic system composed of the bioreactor.

It is specified that the method just described can be used in combination with the system analysing the passage of matter (e.g. cells) of the present invention.

Finally it is clear how the system and method of the present invention are not limited to the study and analysis of cell passage.

Due to the embodiments of the bioreactor, the system and the method of the present invention can further provided, among others, the following applications:
- absorption test for a lotion (cosmetics)
- nutritional absorption test for the gastrointestinal system (nutraceutics)
- cytotoxicity test for particulates with different grain size (toxicology)
- drug absorption test (drug delivery).

BRIEF DESCRIPTION OF THE DRAWINGS

These and other characteristics and advantages of the present invention will be more clear from the following description of some embodiments shown in annexed drawings wherein.

DETAILED DESCRIPTION OF THE PREFERRED EMBODIMENTS

It is specified that the figures annexed to the present patent application describe some embodiments of the bioreactor of the present invention and are shown to better understand characteristics and advantages thereof.

Therefore such embodiments have to be intended for merely illustration purposes and not as a limitation to the inventive concept of the present invention, regarding the provision of a bioreactor with replaceable components and easy to be adapted to the different operating needs.

Figure 1:
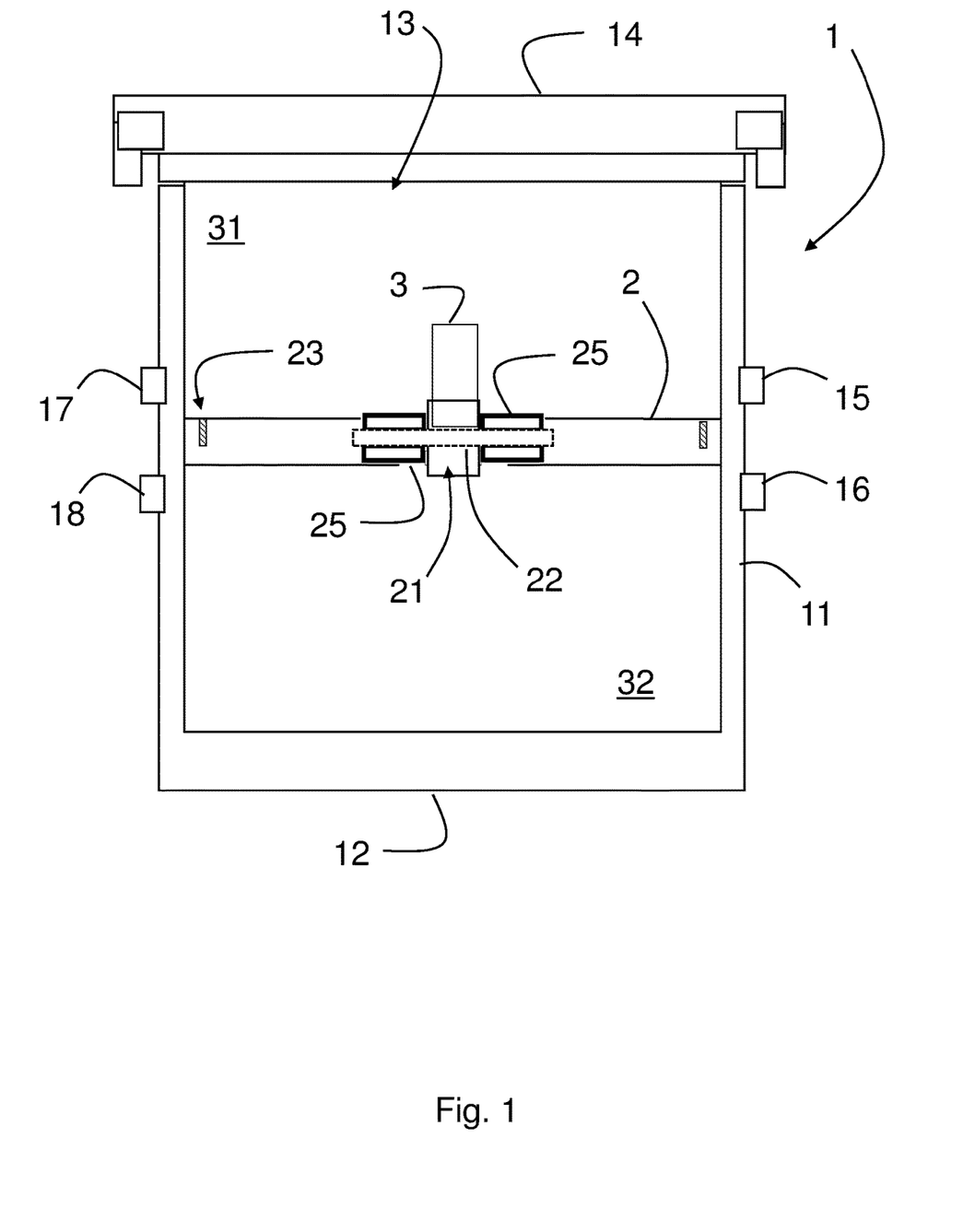
FIG. 1 is a view of a schematic diagram of the bioreactor of the present invention according to one embodiment.

FIG. 1 shows a section of the bioreactor of the present invention, according to a possible embodiment.

The bioreactor 1 comprises a container 1 composed at least of a side wall 11, a bottom wall 12 and an opening 13 closed by a cap 14, such to identify an inner chamber.

Moreover there is provided an intermediate wall 2, placed inside the inner chamber, such to divide the inner chamber in an upper chamber 31 and a lower chamber 32.

The intermediate wall 2 can be made according to different embodiments, shown in FIGS. 1 to 4d.

Such embodiments share the fact that the intermediate wall has a hole 21 intended to house a membrane 22.

The membrane 22 allows cells, molecules, particles, compounds, substances, nutrients, pollutants, growth factors, cell groups (clusters), drugs and/or matter of any kind or electromagnetic radiations to pass from the upper chamber 31 to the lower chamber 32 and vice versa.

In order to carry out analyses of interest and as it will be described below, according to a possible embodiment a sample of biological material 3 is placed in contact with the membrane 22 such to analyze cells belonging to the sample 3 passing through the membrane 22 from the upper chamber 31 to the lower chamber 32.

For practical purposes the hole 21 is placed at the center of the intermediate wall 2, but it can be placed also in an eccentric manner.

Moreover, for the sake of constructional convenience, the container 1 preferably has a cylindrical shape, but it can have any shape without the need of modifying the characteristics of the components described below.

Advantageously the container 1 is composed of plastic material, preferably a biocompatible polymer easy to be sterilized in autoclave, such as polycarbonate or the like.

Preferably the inner chamber has a diameter ranging from 3 centimeters to 5 centimeters, while the side wall 11 has a thickness ranging from 0.7 to 7 millimeters, allowing an optimal compromise to be obtained between mechanical strength, lightness depending on the method used for connecting hydraulic pipes to the system, as it will be described below.

Preferably also the cap 14 and the intermediate wall 2 are composed of a biocompatible polymer material.

As mentioned above the membrane 22 can be composed of a polymer material obtained by electrospinning process.

The intermediate wall 2 is shown in FIG. 1 as horizontally arranged, but obviously it is also possible to provide it to be inclined, depending on operating needs.

With particular reference to FIG. 1 and to FIGS. 4a to 4d the intermediate wall 2 is composed of a plate element fastened to the side wall 11 of the container 1.

Particularly the intermediate wall 2 is composed of an annular element providing the hole 21 at the center.

Moreover the intermediate wall 2 has two threaded holes 23 to allow screws (not shown) to be fastened to remove the intermediate wall 2 from the container 1.

According to a possible embodiment it is possible to provide the intermediate wall 2 to be fastened for example by resting and/or gluing it to two wedges provided in the lower chamber 32 (not shown).

Such wedges can be made as one piece with the intermediate wall 2.

According to the variant shown in FIGS. 4a to 4d, the intermediate wall 2 further has a gasket of the "O-ring" type 24 interposed between the outer wall of the intermediate wall 2 and the inner wall of the container 1.

Such gasket is made of autoclavable and high temperature resistant material and it allows the upper chamber 31 and the lower chamber 32 to be hermetically separated.

Figure 4A:
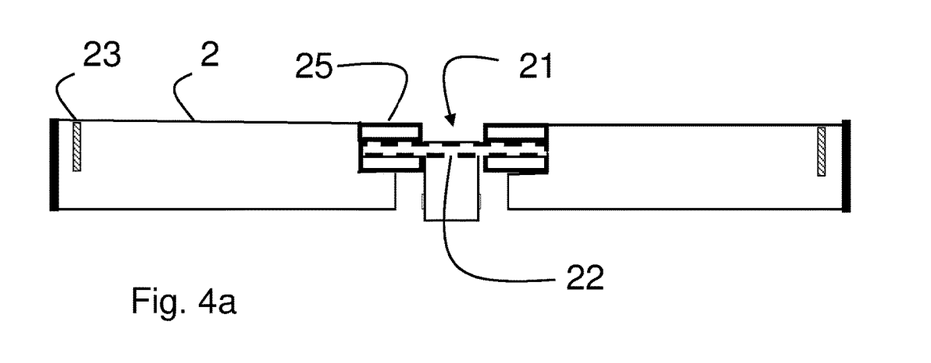
FIGS. 4a to 4d are some details of the components of the bioreactor of the present invention.
Figure 4B:
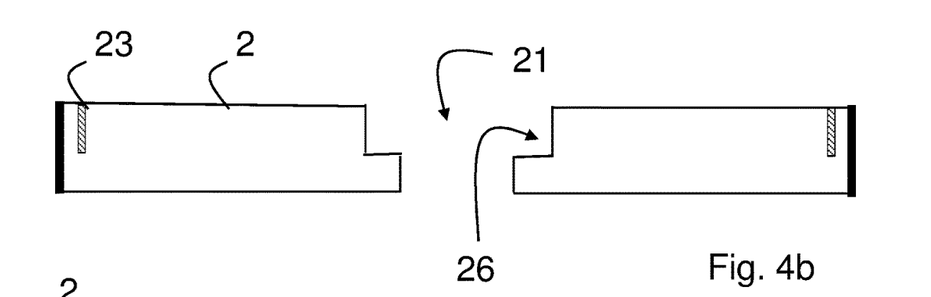

FIGS. 4a and 4b show two side sections of the intermediate wall 2.

Figure 3:
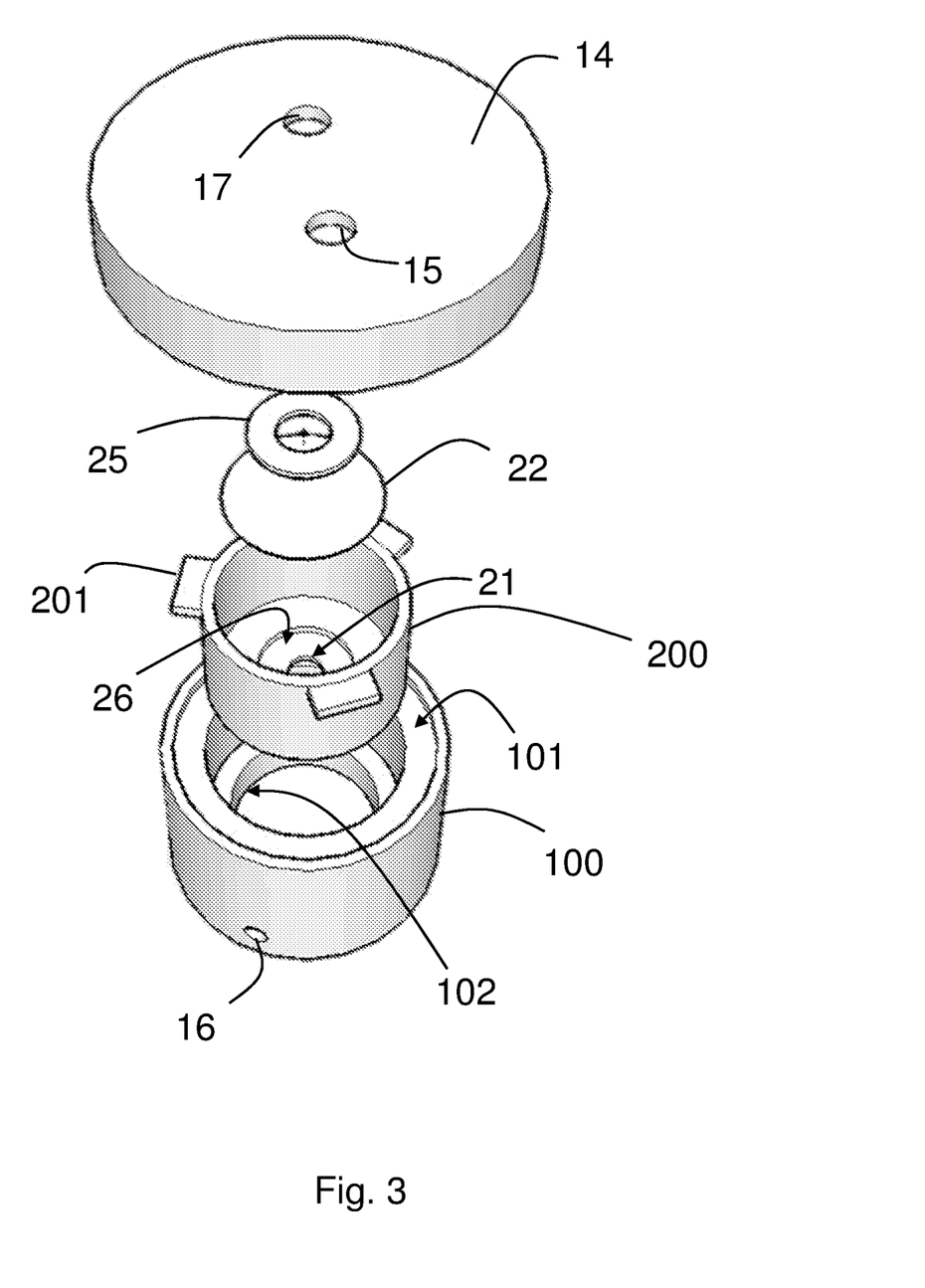
FIG. 3 is an exploded view of the bioreactor of the present invention according to a possible embodiment.

As seen in FIG. 3, the hole 21 is made such to obtain a shoulder intended to form a housing seat 26 where the membrane 22 is inserted.

The membrane 22 can be inserted in the housing seat and possibly it can be fastened, for example by gluing it.

As an alternative, according to the shown embodiment, the membrane 22 is inserted in the housing seat 26 by using removable fastening means composed of two support elements 25 that fasten the membrane 22 in place.

Figure 4C:
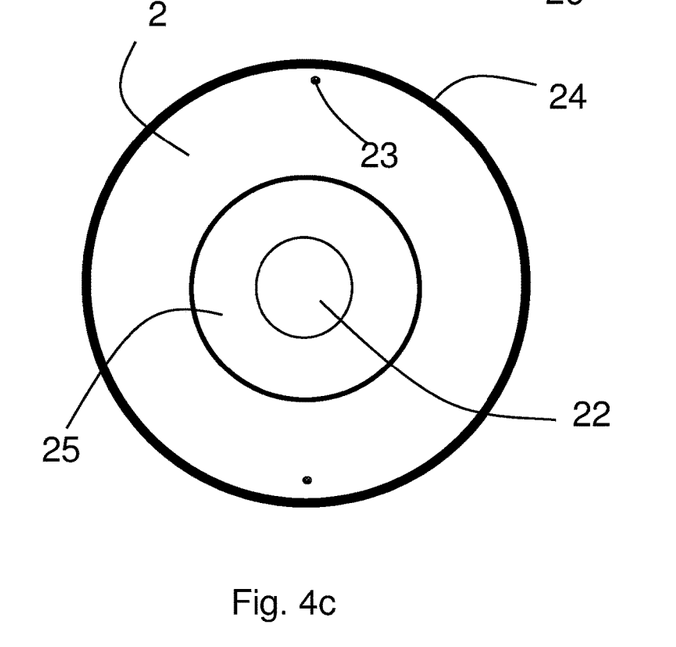
Figure 4D:
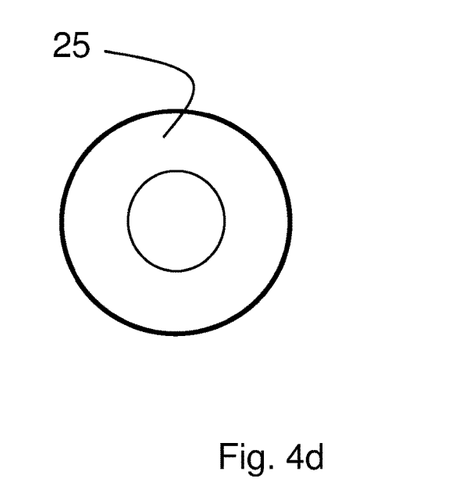

The two jaw elements 25 are preferably composed of two annular elements 25, FIGS. 4c and 4d, that are overlapped, with the membrane 22 being fitted therebetween, such that the membrane 22 can cover the hole of the annular elements 25 and can allow the lower chamber 32 and the upper chamber 31 to be in fluidic communication.

The annular elements 25 can be fastened to the intermediate wall 2 in any of the manners known in prior art.

The annular elements 25 can be further simply placed on the intermediate wall 2, inside the housing seat 26, or can be fastened by means of specific glues.

According to a possible embodiment the annular elements can be made of silicone.

It is possible to provide any number of annular elements 25 and arranged on the basis of operating needs.

As said above, it is possible to provide only one annular support element 25, inserted in the housing seat 26 on which the membrane 22 is placed: in this case the membrane can be simply put on or even glued to the annular support element 25.

As an alternative, such as shown in FIG. 4a, it is possible to provide at least two annular support elements 25 between which the membrane 22 is interposed, a "sandwich" arrangement that is then inserted into the housing seat 26.

According to a possible embodiment it is possible to provide a layer of gluing material interposed between the membrane 22 and one and/or both the annular support elements 25.

According to a further embodiment, as an alternative or in combination with the variant just described, it is possible to provide the membrane 22 to be height adjusted by using a specific number of support elements 25, by simply stacking such support elements 25 inside the housing seat 26 till reaching the desired thickness, then the membrane 22 is rested on the last support element 25.

It is clear how the described configurations do not necessarily require the membrane to be fastened, but it is simply rested.

The remarks just mentioned related to the several configurations of the support elements 25 have been described with reference to the intermediate wall being made as a plate element, but such remarks can be provided in combination with different embodiments of the intermediate wall.

Figure 2A:
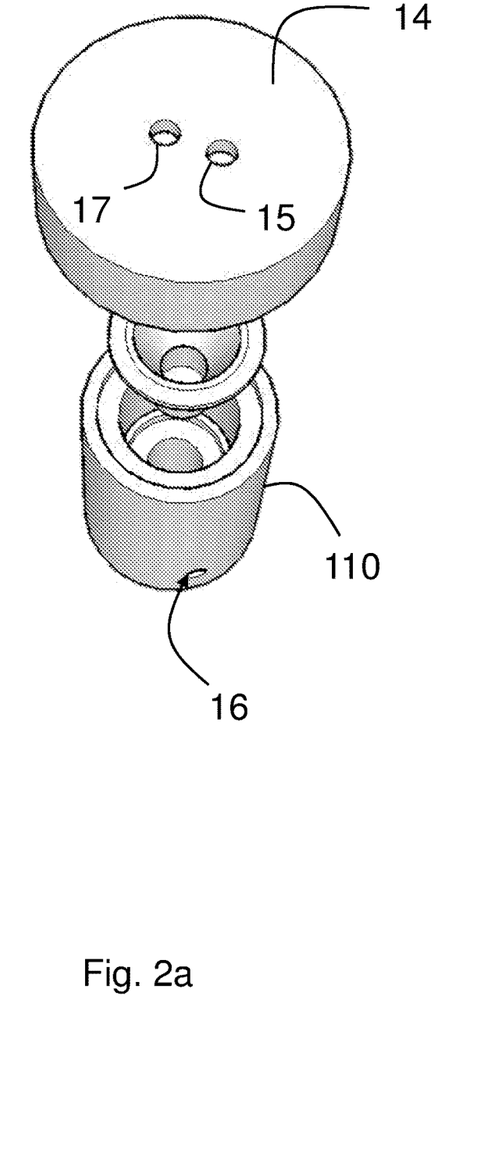
FIGS. 2a and 2b are two exploded views of the bioreactor of the present invention according to a possible embodiment.
Figure 2B:
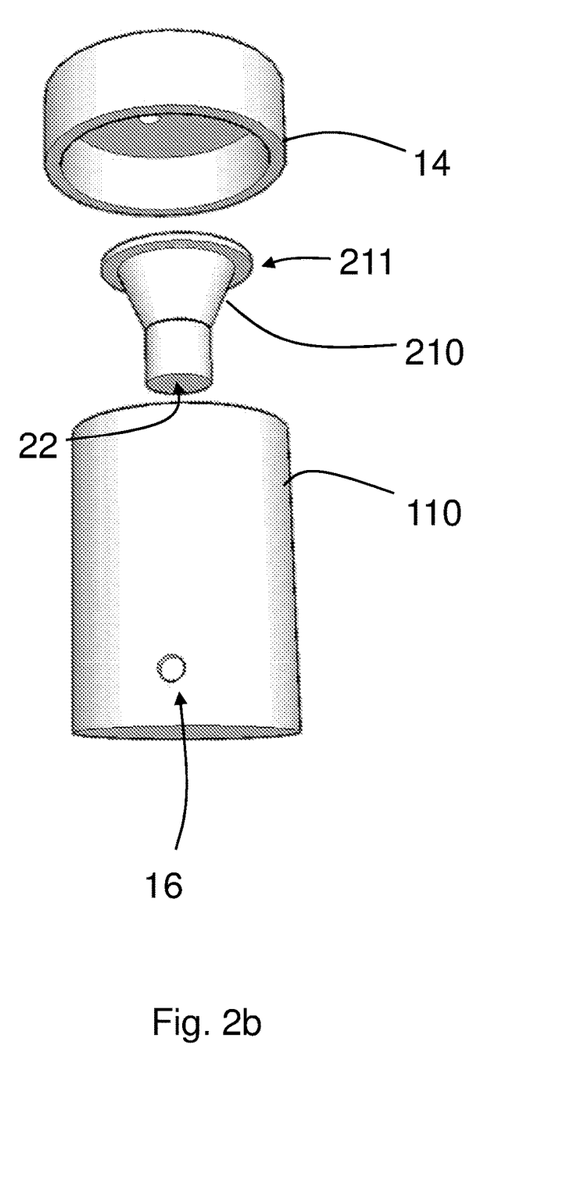

FIGS. 2a to 3 show two possible embodiments, where the intermediate wall is composed of a cup element, wherein the membrane is placed at the bottom wall of the cup.

Particularly FIGS. 2a and 2b show two exploded views of the bioreactor of the present invention, wherein the intermediate wall is composed of a cup element 210 fitted into a container 110.

The fact of fitting the cup element 210 in the container 110 divides the inner chamber of the container 110 in two chambers, a lower chamber, delimited by inner wall of the container 110 and by outer walls of the cup element 210, and a upper chamber delimited by the inner chambers of the cup element 210 and by the cap 14.

The cup element 210 has an upper protruding rim 211 that, in the fitted condition, contacts a step shoulder obtained inside the container 110 and visible in FIG. 2a.

Both the protruding rim and the cup element can provide any shape, different from the circular or cylindrical shape shown in the figure.

Moreover the protruding rim can also be discontinuous, that is not provided all along the diameter of the cup element, by providing protruding rim portions allowing the function thereof to be accomplished.

Therefore in the fitted condition the passage from the upper chamber to the lower chamber and vice versa is possible only through the membrane 22, that can be housed at the bottom of the cup element 210.

As an alternative it is possible to provide the membrane 22 to be made as one piece with the cup element 210.

With reference to FIG. 3, the bioreactor has a cup element 200 where the housing seat 26 for the membrane 22 is formed in the thickness of the bottom.

Inside the housing seat 26 it is possible to provide one or more annular support elements 25, according to configurations described above.

Moreover the cup element 200 has some appendages 201 at the upper rim, for example but not necessarily three appendages.

With the cup element 200 in the condition fitted into the container 100, such appendages 201 are in contact with the seat 101 obtained in the thickness of the side walls of the container 100.

Moreover the bottom of the cup element 200 in the fitted condition is in contact with the step 102, obtained on the side walls of the container 100.

Therefore advantageously the outer diameter of the cup element 200 corresponds to the inner diameter of the container 100, such that the lower chamber of the bioreactor is delimited below by the bottom wall of the container 100 and at the top by the bottom wall of the cup element 200, while the upper chamber is delimited by the inner surfaces of the cup element 200 and by the cap 14.

Regardless of the realization of the cup element, it is possible to provide means for height adjusting it by using for example shims cooperating with the rim 211 or with appendages 201.

Figure 5A:
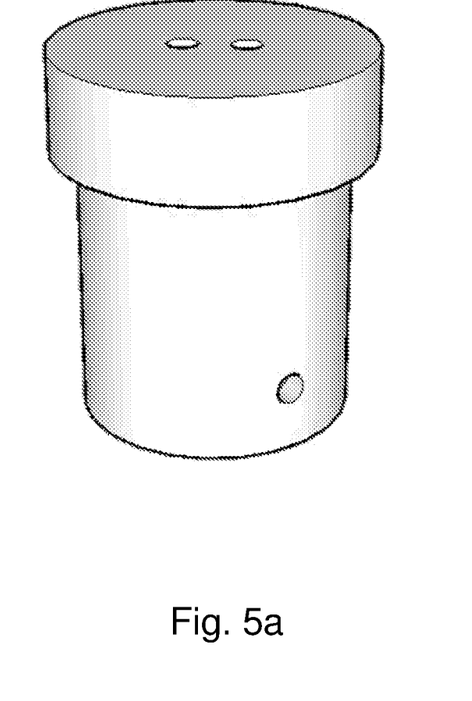
FIGS. 5a and 5b are two views of the bioreactor in the closed condition.
Figure 5B:
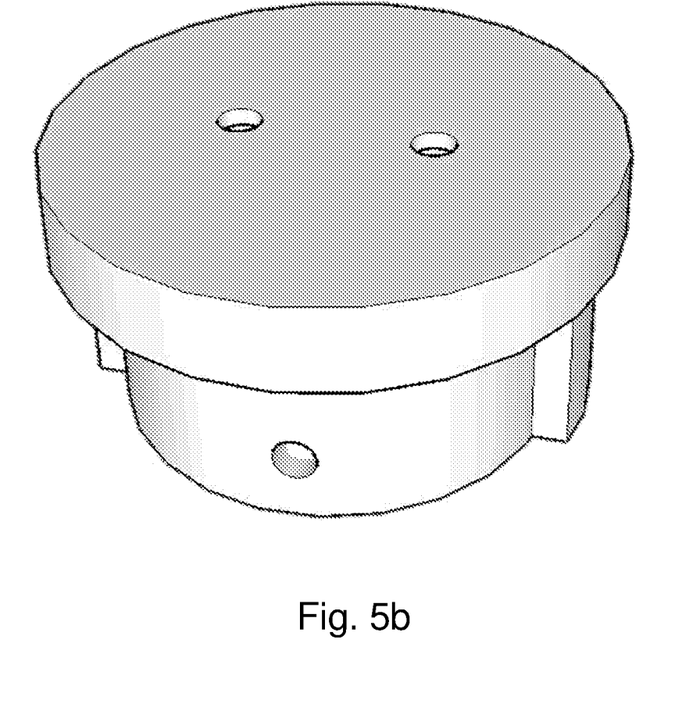

FIGS. 5a and 5b show two views of the bioreactor in the closed condition, according to variant embodiments of FIGS. 2a-2b and 3 respectively.

Figure 7A:
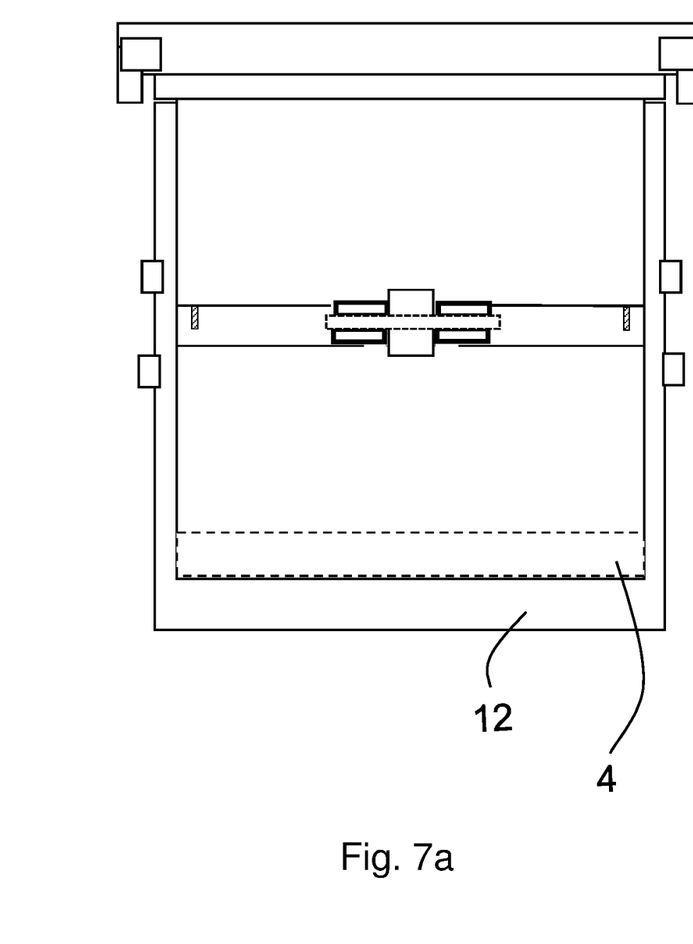
FIGS. 7a and 7b are the bioreactor of the present invention according to a possible variant embodiment.
Figure 7B:
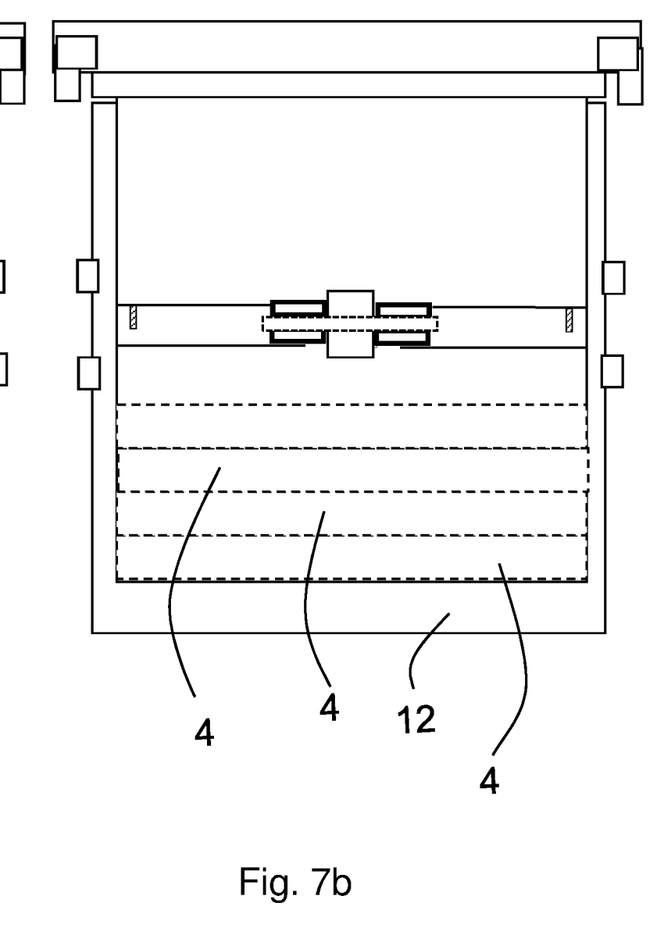

FIGS. 7a and 7b show a further variant embodiment of the bioreactor of the present invention, according to which it is possible to provide at least one plate element 4, insertable within the lower chamber 32 to adjust the volume thereof.

The plate element 4 can have any size and shape, suffice that is serves the function of occupying part of the volume of the lower chamber 32.

According to the embodiment shown in FIGS. 7a and 7b the plate element 4 has a specific thickness and a shape corresponding to the bottom wall 12, such that different plate elements 4 can be stacked on each other, such as shown in FIG. 7b.

The characteristics of the bioreactor described above, allow the bioreactor to have a high adaptability to operating needs, therefore it is clear that it is possible to reduce the volume of the lower chamber not only by means of the plate elements, but also by modifying the shape of the lower chamber.

With reference again to FIGS. 1 to 3, it is possible to note how the side wall 11 delimiting the upper chamber 31 and the side wall 11 delimiting the lower chamber 32 have at least one inlet port 15, 16 and at least one outlet port 17, 18 for the connection of corresponding hydraulic circuits.

Inlet ports 15, 16 and outlet ports 17, 18 can be placed in any manner and position along the side wall 11 or lower wall 12.

In the particular case of FIGS. 7a and 7b it is clear how it is better to place the ports 16 and 18 for the lower chamber 32 near the intermediate wall, to prevent that the positioning of plate elements 4 may interfere with the fluid flow.

As an alternative it is possible to provide the inlet port 15 and outlet port 17 of the upper chamber 31 to be inserted on the cap 14, such as shown in FIGS. 2a, 2b and 3.

Figure 6A:
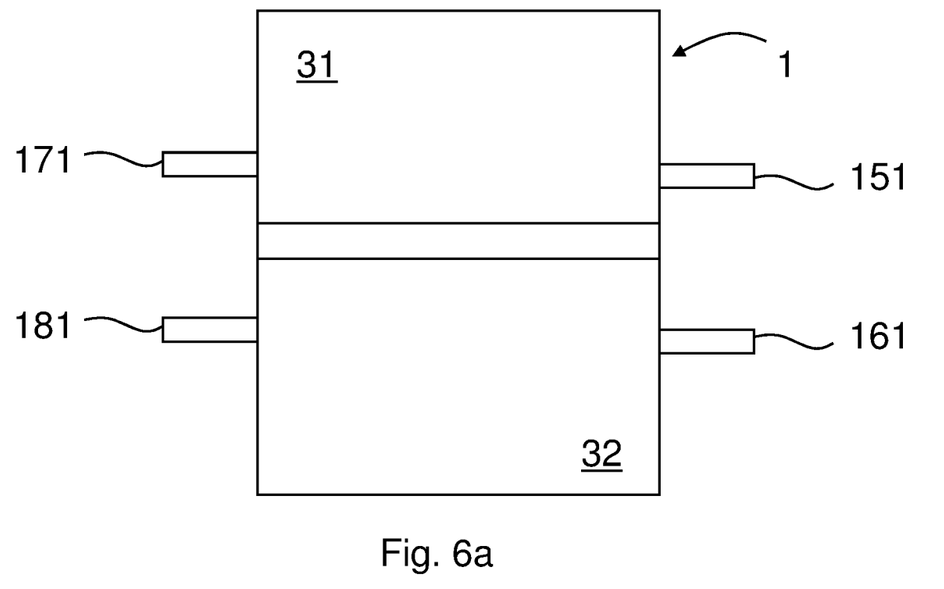
FIGS. 6a and 6b are two possible configurations of the connection between hydraulic circuit and bioreactor of the present invention.
Figure 6B:
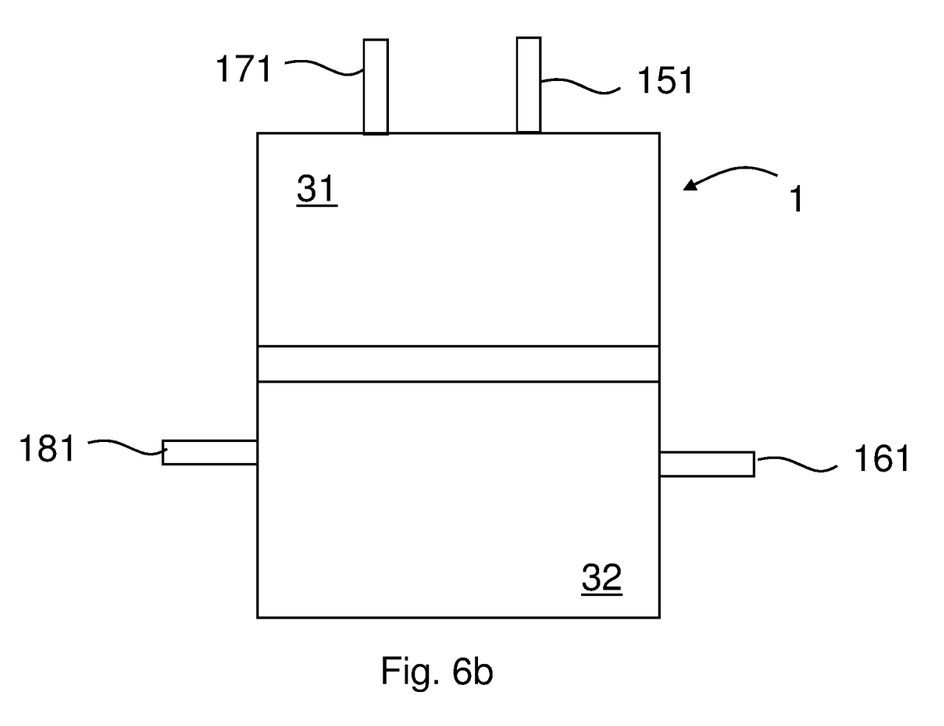

FIGS. 6a and 6b schematically show a possible configuration of the hydraulic circuits connected to inlet and outlet ports.

Particularly there is provided a pipe 151 and a pipe 161 connected to inlet ports 15 and 16 of the upper chamber 31 and lower chamber 32 respectively and a pipe 171 and a pipe 181 connected to outlet ports 17 and 18 of the upper chamber 31 and lower chamber 32 respectively.

In FIG. 6a the pipes 151 and 171 of the upper chamber 31 are connected to the side wall of the container 1, while in FIG. 6b the pipes 151 and 171 are provided on the cap 14.

Pipes 161 and 181 for the lower chamber 32, for constructional simplicity, are always connected to the side wall of the container 1, but they have not to be necessarily along the same axis, they can be also on different planes or axes, for example on the same plane, but with axes inclined by a specific angle.

The connection with a hydraulic circuit, some embodiments thereof being described below, can occur by closing the outlet pipe 171 of the upper chamber 31 and the inlet pipe 161 of the lower chamber 32.

Thus the hydraulic circuit will have only one delivery pipe 151, inlet of the upper chamber 31, and only one return pipe 181, outlet of the lower chamber 32, such to force the flow to pass through the interface membrane (perfusion).

Figure 8:
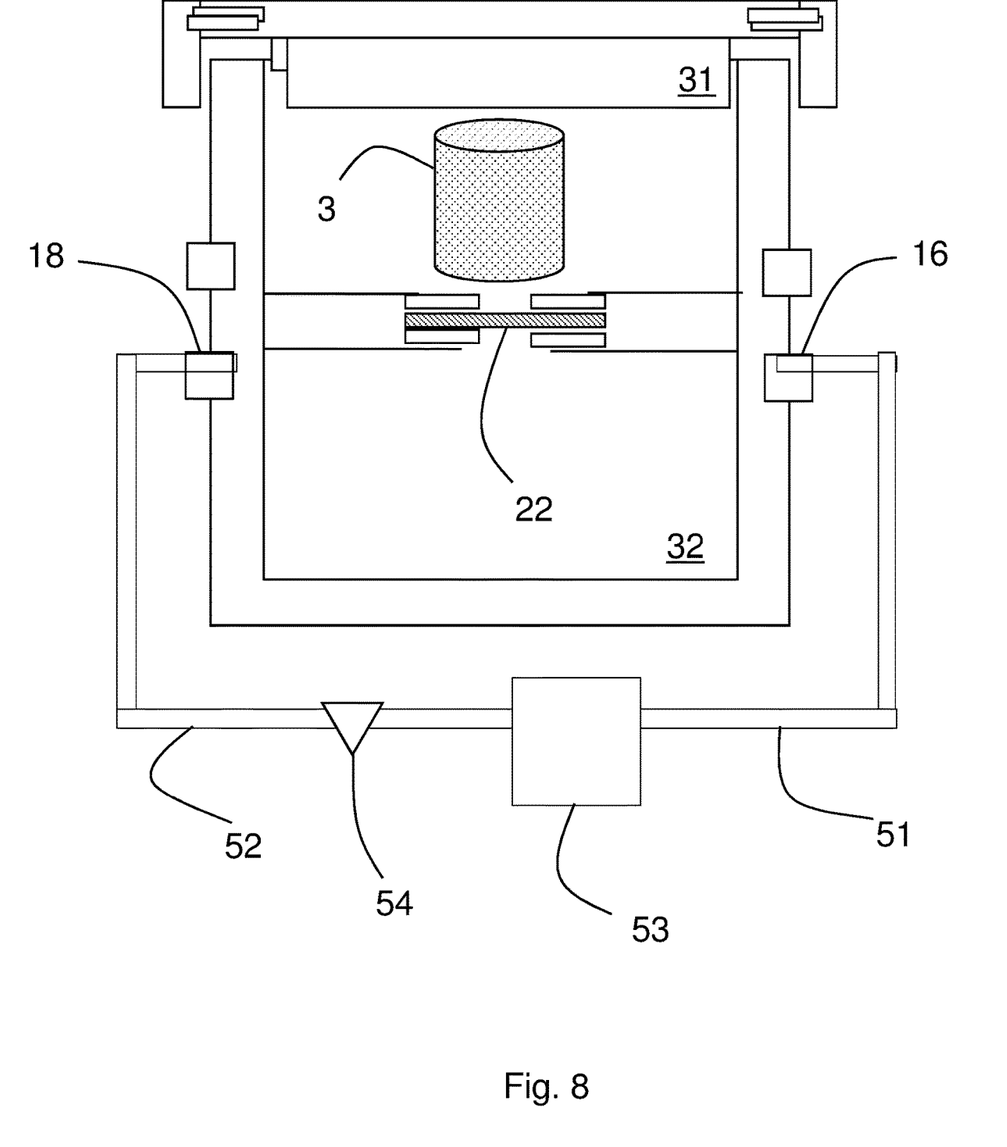
FIG. 8 is the bioreactor of the present invention in combination with a hydraulic circuit.

FIG. 8 shows the use of the bioreactor of the present invention.

According to such embodiment there is provided a hydraulic circuit connected to the lower chamber 32.

The hydraulic circuit has a delivery pipe 51 connected to the inlet port 16, a return pipe 52 connected to the outlet port 18 and a pump 53 operating the flow of a fluid inside the circuit.

The return pipe 52 further has a three-way valve 54, but any type of valve can be provided allowing at least a part of the circulating fluid to be sampled.

A completely similar hydraulic circuit can be provided also in connection to the upper chamber 31.

With particular reference to FIG. 8, the sample 3 is placed in contact with the membrane 22, the pump 53 generates a flow flowing in the hydraulic circuit and the three-way valve 54 allows to sample a part of the flowing fluid.

On the drawn part of the fluid, some analyses can be performed, such to evaluate the concentration of cells belonging to the sample 3 to study the passage of cells through the membrane 22.

The sample 3 can be composed of an engineered material, or a biological tissue (for example biopsy) and can be cultured in the bioreactor in close contact with the membrane 22.

As set forth, the set-up with reference to FIG. 8 is particularly functional for studying diffusion of tumor cells in the body.

Figure 9:
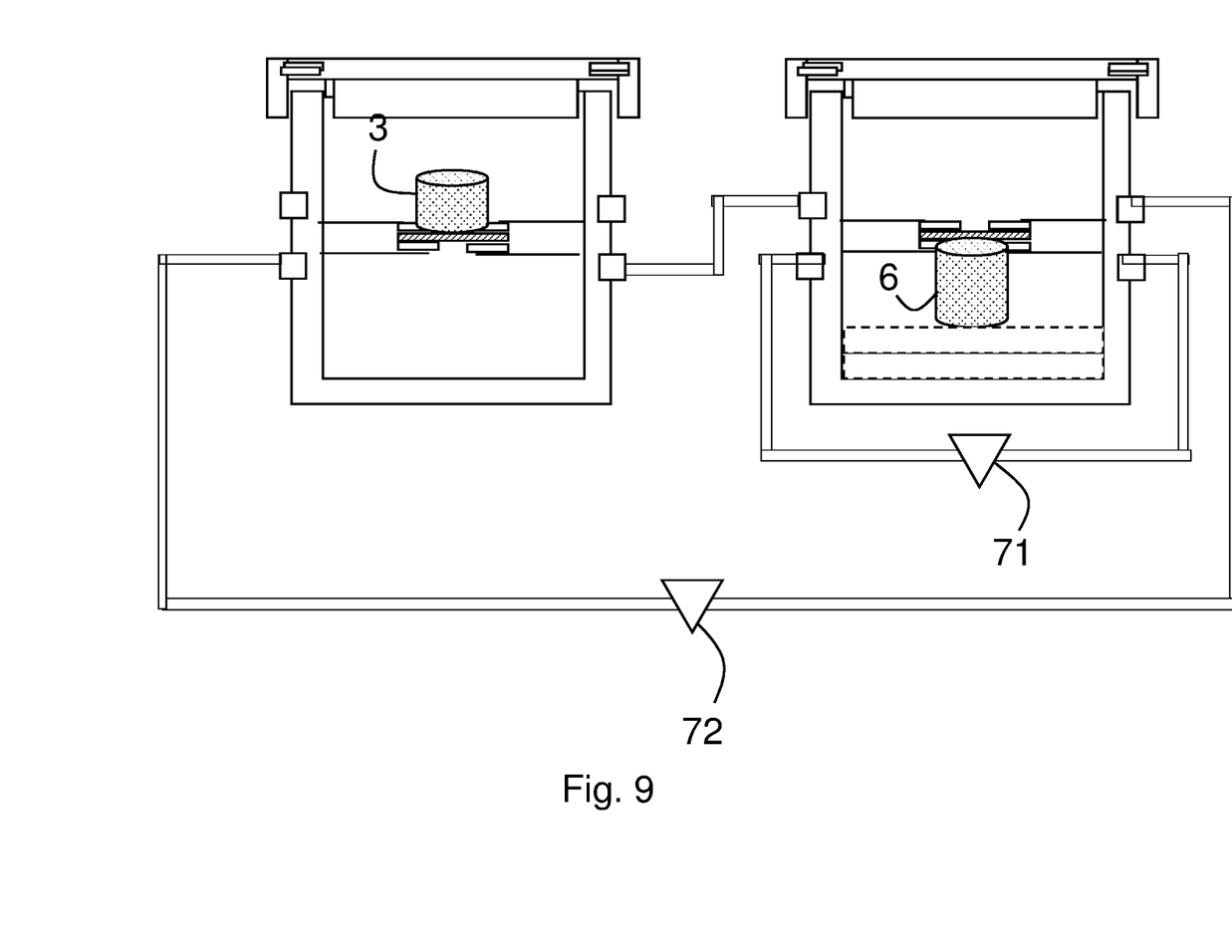
FIG. 9 is the system analysing the cell passage in the metastasis model of the present invention.

With the same aim it is possible to make the set-up shown in FIG. 9, intended to show the system analysing the passage of cells or molecules of biological interest (e.g. drugs) according to the present invention.

FIG. 9 shows two bioreactors connected in series, wherein the inlet ports and outlet ports of the lower chamber 32 of the bioreactor on the left are connected to the outlet and inlet ports respectively of the upper chamber 31 of the bioreactor on the right.

Moreover the inlet and outlet ports of the lower chamber 32 of the bioreactor on the right have a hydraulic circuit completely similar to that of FIG. 8.

Unlike the arrangement of FIG. 8, FIG. 9 shows also a further sample, or target organ 6 in the bioreactor on the right, that can be connected in contact with the membrane 22.

By sampling the fluid flowing through the valves 71 and 72, therefore it will be possible to evaluate not only the passage of the sample 3 through the membrane 22, but also to study the migration and adhesion of such cells to the target organ 6, as well as to study the effect of the passage of molecules of biological interest through the membrane 22.

As an alternative to the variant just described, it is possible to provide the target organ 6 to be provided in the upper chamber of the second bioreactor, such to evaluate the passage of cells of the sample 3 to the target organ 6 simply though a single barrier, represented by the membrane inserted in the first bioreactor.

As set forth, therefore it is possible by the system of FIG. 9 to evaluate the growth of a tumor in vitro.

Moreover by using the characteristics of the bioreactor of the present invention, it is possible for example to provide to insert drugs inside the hydraulic circuit to carry out preventive analyses for treating tumors grown in vitro, or other types of analyses or studies on tumors.

Finally a particularly important application of the bioreactor of the present invention is related to the use of membranes intended to simulate the skin.

In this case it is possible to evaluate how much toxic agents, pollutants, various particles or molecules, drugs or active principles or radiations (e.g. UV radiations) are able to pass through the skin and to pass in surrounding tissues and when the use of possible drugs or cosmetic solutions (for example lotions) modify such passage.

In order to carry out such method it is possible to create a fluid flow containing particles or molecules under examination (for example pollutants, or drugs or other molecules) in the upper chamber and flow of clean fluid in the lower chamber.

The membrane can be composed of human or animal skin or natural or artificial tissues, intended to simulate the human skin.

Finally cosmetic or dermatologic solutions are used placed on the membrane and, on the basis of their different types, the transmission of pollutants and/or of external agents from the upper chamber to the lower chamber is evaluated.

A possible use of the bioreactor of the present invention involving the study of diffusion of substances through the skin, but not limited to cosmetics, but related to pharmacology, for example is the analysis of the amount of lotions, creams or the like that, once spread on the skin, pass at systemic level and is absorbed by the organism.

Finally it is clear how the bioreactor of the present invention allows different applications to be obtained besides the ones described herein.

For example it is possible to use the bioreactor with epithelial tissues different from skin, such as lung barrier, gastrointestinal barrier, cornea, urethra or other epithelial tissues and not epithelial tissues.

In the case of the lung barrier it is possible to use the bioreactor to evaluate how much an external agent spreads into the organism passing though the lung barrier.

As regards gastrointestinal barrier, the bioreactor of the present invention is widely used in nutraceutical field, making it possible to analyse how much a substance can be absorbed by the organism and which amounts.

Another use, still with reference to the passage of specific substances through the gastrointestinal barrier, may be related to digestibility of such substances.

The invention claimed is:

1. A bioreactor comprising a container having at least one side wall, a bottom wall and an opening closed by a cap to define an inner chamber,
   an intermediate wall inside said inner chamber to divide said inner chamber in an upper chamber and a lower chamber,
   said intermediate wall comprising a membrane,
   wherein said intermediate wall is mounted to said bottom wall and/or said side wall,
   said intermediate wall comprising a shoulder forming a housing seat to house said membrane;
   a plurality of like interchangeable stackable annular support elements having planar support surfaces, said membrane being interposed between two of the support elements in a sandwiched arrangement including one or more of the support elements below said membrane and a single one of the support elements above the membrane, wherein the sandwiched arrangement of the support elements and the membrane is inserted into the housing seat, and wherein a quantity of the one or more support elements below the membrane comprises a variable quantity of the support elements to position the membrane at a selectable height;
   an inlet port and an outlet port, wherein the ports are open to connect to hydraulic circuits, or the ports are closed by a polymer septum to connect to a syringe; the inlet port and the outlet port being formed in the at least one side wall, in the at least one cap or in the bottom wall.

2. Bioreactor according to claim 1, wherein said intermediate wall comprises a cup element, and the membrane is at a bottom of the cup element.

3. Bioreactor according to claim 2, wherein said cup element at an upper rim has at least one protruding region resting on said side wall.

4. Bioreactor according to claim 2, wherein said housing seat is formed in the bottom of said cup element.

5. Bioreactor according to claim 4, wherein one of the support elements is perforated at the center, the perforated support element is inserted into said housing seat, said membrane resting on said perforated support element.

6. Bioreactor according to claim 1, comprising a layer of gluing material interposed between said membrane and said support elements.

7. Bioreactor according to claim 2, wherein said membrane is made as one piece with said cup element.

8. Bioreactor according to claim 1, comprising means for height adjustment of said cup element.

9. Bioreactor according to claim 1, comprising at least one plate element with a specific thickness and shape, the plate element being in contact with said bottom wall to limit volume of the lower chamber.

10. Bioreactor according to claim 1, comprising at least one fluidic circuit connected to said lower chamber and/or to said upper chamber,
    the fluidic circuit having at least one pump, a delivery pipe and return pipe.

11. Bioreactor according to claim 10, wherein said delivery pipe and/or said return pipe and/or said ports have at least one valve or point of access for drawing at least a part of the flowing fluid.

12. Bioreactor according to claim 1, wherein the cap has a seal for liquid and/or gaseous fluids.

13. Bioreactor according to claim 1, comprising one or more sensors inside or outside the lower chamber and/or upper chamber and/or walls delimiting the bioreactor.

14. Bioreactor according to claim 1, wherein said membrane is made at least partially of cells of living tissue.

15. System for detecting and analysing passage and/or absorption of cells, molecules, particles, compounds, substances, nutrients, pollutants, growth factors, cell clusters, drugs and/or matter of any kind or electromagnetic radiations, the system comprising a plurality of said bioreactors according to claim 1, the bioreactors are connected with one another through a fluidic circuit.

16. The system according to claim 15, wherein said system comprises at least two of said bioreactors including a first bioreactor and a second bioreactor, wherein the upper chamber of the first bioreactor is configured to contain tumor tissues or cells, biopsies, or decellularized materials or cell clusters, and the upper chamber or the lower chamber of the second bioreactor is configured to contain a metastasizable target, as an ex vivo/in vitro metastasis model.

17. The system according to claim 15, wherein said system comprises at least two of said bioreactors including a first bioreactor and a second bioreactor, wherein the upper chamber and/or the lower chamber of the first bioreactor and/or the second bioreactor are configured to receive one or more injected drugs or molecules of interest, as an ex vivo/in vitro disease model for research, safety and efficacy studies, pharmacokinetic and pharmacodynamics studies, drug discovery, and/or drug repositioning.

18. The system according to claim 15, wherein said system comprises at least two of said bioreactors including a first bioreactor and a second bioreactor, wherein the upper chamber and/or the lower chamber of the first bioreactor and/or the second bioreactor are configured to receive one or more injected drugs or molecules for therapeutic use.

19. Bioreactor according to claim 1, wherein the bioreactor comprises a first configuration with one of the support elements below the membrane, and a second configuration with at least two of the support elements below the membrane.

20. Bioreactor according to claim 1, wherein the support elements comprise planar upper and lower support surfaces.

* * * * *